(12) United States Patent
Allier et al.

(10) Patent No.: US 10,481,076 B2
(45) Date of Patent: Nov. 19, 2019

(54) METHOD FOR DETERMINING THE STATE OF A CELL

(71) Applicants: COMMISSARIAT A L'ENERGIE ATOMIQUE ET AUX ENERGIES ALTERNATIVES, Paris (FR); IPRASENSE SAS, Clapiers (FR); HORIBA ABX SAS, Montpellier (FR)

(72) Inventors: Cedric Allier, Grenoble (FR); Geoffrey Esteban, Teyran (FR); Lionel Herve, Corenc (FR)

(73) Assignees: COMMISSARIAT A L'ENERGIE ATOMIQUE ET AUX ENERGIES ALTERNATIVES, Paris (FR); IPRASENSE SAS, Clapiers (FR); HORIBA ABX SAS, Montpellier (FR)

( * ) Notice: Subject to any disclaimer, the term of this patent is extended or adjusted under 35 U.S.C. 154(b) by 26 days.

(21) Appl. No.: 15/560,694

(22) PCT Filed: Mar. 23, 2016

(86) PCT No.: PCT/FR2016/050644
§ 371 (c)(1),
(2) Date: Sep. 22, 2017

(87) PCT Pub. No.: WO2016/151249
PCT Pub. Date: Sep. 29, 2016

(65) Prior Publication Data
US 2018/0113064 A1    Apr. 26, 2018

(30) Foreign Application Priority Data

Mar. 24, 2015    (FR) ...................................... 15 52445

(51) Int. Cl.
*G01N 15/14*    (2006.01)
*C12M 1/34*    (2006.01)
(Continued)

(52) U.S. Cl.
CPC ......... *G01N 15/1463* (2013.01); *C12M 41/46* (2013.01); *G01N 15/1429* (2013.01);
(Continued)

(58) Field of Classification Search
CPC .............. C12M 41/46; G01N 15/1429; G01N 15/1431; G01N 15/1463; G01N 15/1475;
(Continued)

(56) References Cited

U.S. PATENT DOCUMENTS

2009/0290156 A1    11/2009  Popescu et al.
2012/0105858 A1    5/2012   Popescu et al.
(Continued)

FOREIGN PATENT DOCUMENTS

WO    2014/012031 A1      1/2014
WO    WO 2014/012031 A1 *  1/2014

OTHER PUBLICATIONS

International Search Report dated Jul. 15, 2016 in PCT/FR2016/050644 filed Mar. 23, 2016.
(Continued)

*Primary Examiner* — Edward Park
(74) *Attorney, Agent, or Firm* — Oblon, McClelland, Maier & Neustadt, L.L.P.

(57) ABSTRACT

A method for identifying a state of a cell contained in a sample, including: illuminating the sample using a light source by producing an incident light wave propagating toward the sample; then acquiring, using a matrix-array photodetector, an image of the sample, the sample being placed between the light source and the matrix-array photodetector such that the matrix-array photodetector is exposed to a light wave resulting from interference between the incident light wave and a diffraction wave produced by each cell; applying a numerical reconstruction algorithm to the image acquired by the matrix-array photodetector, to (Continued)

estimate a characteristic quantity of the light wave reaching the matrix-array detector, at a plurality of distances from the matrix-array photodetector. The value of the characteristic quantity, or its variation as a function of distance, allows the state of the cell to be determined from among predetermined states.

15 Claims, 7 Drawing Sheets

(51) Int. Cl.
| | | |
|---|---|---|
| *G01N 21/45* | (2006.01) | |
| *G01N 21/47* | (2006.01) | |
| *G01N 21/51* | (2006.01) | |
| *G03H 1/08* | (2006.01) | |
| *G06K 9/00* | (2006.01) | |
| *G06T 7/00* | (2017.01) | |
| *G03H 1/04* | (2006.01) | |
| *G01N 33/483* | (2006.01) | |
| *G01N 15/10* | (2006.01) | |
| *G01N 21/17* | (2006.01) | |
| *G03H 1/00* | (2006.01) | |
| *G01N 15/00* | (2006.01) | |

(52) U.S. Cl.
CPC ..... *G01N 15/1431* (2013.01); *G01N 15/1475* (2013.01); *G01N 21/453* (2013.01); *G01N 21/4788* (2013.01); *G01N 21/51* (2013.01); *G01N 33/4833* (2013.01); *G03H 1/0443* (2013.01); *G03H 1/0866* (2013.01); *G06K 9/0014* (2013.01); *G06K 9/00134* (2013.01); *G06K 9/00147* (2013.01); *G06T 7/0012* (2013.01); *G01N 2015/0065* (2013.01); *G01N 2015/1006* (2013.01); *G01N 2015/1445* (2013.01); *G01N 2015/1454* (2013.01); *G01N 2021/1772* (2013.01); *G01N 2021/1782* (2013.01); *G03H 2001/005* (2013.01); *G03H 2001/0447* (2013.01); *G03H 2001/0454* (2013.01); *G03H 2001/0825* (2013.01); *G03H 2222/22* (2013.01); *G06T 2200/04* (2013.01); *G06T 2207/10024* (2013.01); *G06T 2207/10056* (2013.01); *G06T 2207/10064* (2013.01); *G06T 2207/30024* (2013.01)

(58) Field of Classification Search
CPC .. G01N 21/453; G01N 21/4788; G01N 21/51; G01N 33/4833; G01N 2015/0065; G01N 2015/1006; G01N 2015/1445; G01N 2015/1454; G01N 2021/1772; G01N 2021/1782; G03H 1/0443; G03H 1/0866; G03H 2001/005; G03H 2001/0447; G03H 2001/0454; G03H 2001/0825; G03H 2222/22; G06K 9/00134; G06K 9/0014; G06K 9/00147; G06T 7/0012; G06T 2200/04; G06T 2207/10024; G06T 2207/10056; G06T 2207/10064; G06T 2207/30024

See application file for complete search history.

(56) References Cited

U.S. PATENT DOCUMENTS

| | | |
|---|---|---|
| 2012/0148141 A1 | 6/2012 | Ozcan et al. |
| 2013/0258091 A1 | 10/2013 | Ozcan et al. |
| 2014/0133702 A1 | 5/2014 | Zheng et al. |
| 2014/0327944 A1 | 11/2014 | Naidoo et al. |
| 2014/0365161 A1 | 12/2014 | Naidoo et al. |
| 2015/0204773 A1 | 7/2015 | Ozcan et al. |

OTHER PUBLICATIONS

International Search Report dated Jun. 20, 2016 in PCT/FR2016/050643 filed Mar. 23, 2016.

S. Vinjimore Kesavan et al., "High-throughput monitoring of major cell functions by means of lensfree video microscopy," Scientific Reports, vol. 4, Aug. 6, 2014, pp. 1-11, XP055250876.

Karen M. Molony et al., "Segmentation and visualization of digital in-line holographic microscopy of three-dimensional scenes using reconstructed intensity images," Medical Imaging 2002: PACS and Integrated Medical Information Systems: Design and Evaluation, vol. 7443, Aug. 20, 2009, pp. 74431F-1-74431F-10, XP055251117.

Sergey Missan et al., "Using digital inline holographic microscopy and quantitative phase contrast imaging to assess viability of cultured mammalian cells," Progress in Biomedical Optics and Imaging, SPIE—International Society for Optical Engineering, vol. 9336, Mar. 11, 2015, pp. 93316X-1-93316X-14, XP060049373.

Yunxin Wang et al., "Non-invasive monitoring for living cell culture with lensless Fourier transform digital holography microscopy," Medical Imaging 2002: PACS and Integrated Medical Information Systems: Design and Evaluation, vol. 7791, Aug. 2, 2010, pp. 77910E-1-77910E-8, XP055250808.

Bjorn Kemper et al., "Application of 3D tracking, LED illumination and multi-wavelength techniques for quantitative cell analysis in digital holographic microscopy," Engineering of SPIE, SPIE—International Society for Optical Engineering, vol. 7184, Jan. 2009, XP007913134, pp. 71840R-1-71840R-12.

\* cited by examiner

METHOD FOR DETERMINING THE STATE OF A CELL

TECHNICAL FIELD

The invention relates to the field of analysis of cells, and more precisely to the inspection of the proliferation of cells, in incubators or biological reactors.

PRIOR ART

The inspection of the development of cells in incubators or biological reactors is an essential step in the process of producing cells. In these applications, the cells are placed in a culture medium, propitious to their development.

Their number and their state, and in particular whether they are alive or dead, are regularly inspected. These inspecting operations require the use of a microscope, the cells being marked beforehand using a fluorescent tag or a chromophore, the level of fluorescence of cells varying depending on whether they are alive or dead. Such a method has certain drawbacks: firstly, it requires the use of a microscope, a piece of equipment that is costly and bulky. In addition, since the field of observation is small, the analysis of a spatially extensive sample requires time because it is necessary to move the sample in front of the microscope. Moreover, marking cells with a fluorescent label or a chromophore may have consequences on their development.

One of the pursued avenues of research is the use of simple optical methods, such as lensless imaging. The observation of biological particles by lensless imaging has seen a certain amount of development since the end of the years 2000. This technique consists in placing a sample between a light source and a matrix-array photodetector or image sensor. The image captured by the photodetector is formed by interference between the incident wave, produced by the light source, and the wave diffracted by the particles making up the sample. This image is frequently referred to as a "hologram". Thus, for each particle, it is possible to record, on the sensor, a diffraction pattern that is specific thereto. Applied to biological samples, this technique has been described in document WO2008090330. It is then possible to perform a simple analysis of each particle, by comparing the diffraction pattern that it generates with diffraction patterns established beforehand and corresponding to known particles. However, this method may reach limits as particle concentration increases.

It is possible to apply mathematical techniques i.e. what are referred to as digital holographic reconstruction techniques, in order to construct what is called a complex image of each particle present in the sample. This type of technique consists in back-propagating the light wave to the object plane, in which the particles are located, said object plane being located a known distance from the image. Applications to the characterization of cells on the basis of a reconstructed complex image have been described in the documents US2012/0148141 and WO2014/012031, the cells being spermatozoa. However, these methods are limited to estimation of the properties of said cells, and their path, from the reconstructed complex image. A complex image of a sample may be insufficient to identify a particle.

Therefore what is sought is a method for observing cells, and in particular a means for discriminating living and dead cells, which is simple, inexpensive, reliable, does not require cells to be marked and has an extensive field of observation.

DISCLOSURE OF THE INVENTION

The invention responds to this problem by providing a method for determining the state of a cell, said cell being placed in a sample, the method including the following steps:
illuminating said sample using a light source, the light source producing an incident light wave propagating towards the sample along a propagation axis;
acquiring, using a matrix-array photodetector, an image of the sample, the sample being placed between said light source and said matrix-array photodetector in such a way that the matrix-array photodetector is exposed to a light wave comprising interference between the incident light wave and a diffraction wave produced by each cell;
determining a position of said cell in a plane parallel to a detection plane in which the matrix-array photodetector lies;
applying a digital reconstruction algorithm to said acquired image, so as to determine at least one characteristic quantity of the light wave to which the matrix-array photodetector is exposed, at said position, at a plurality of what are called reconstruction distances from said photodetector along said propagation axis; and
classifying the cell depending on a profile representing a variation in said characteristic quantity along the propagation axis, this classification allowing the state of said cell to be determined from among preset states.

The profile is defined depending on the value of the characteristic quantity and determined at said plurality of distances.

In particular, the preset states may comprise a living state and a dead state. The method is then able to classify an examined cell and determine whether it is dead or alive.

By applying a digital reconstruction algorithm, what is meant is the application of a propagation operator to an image, generally in the form of a convolution product.

Each characteristic quantity is in particular obtained by estimating, at said reconstruction distance, a complex expression of the light wave to which the matrix-array photodetector is exposed. The characteristic quantity may be obtained from the modulus or argument of said complex expression.

The classification may be carried out by comparing said variation in said characteristic quantity to preset reference profiles.

According to one embodiment, the method includes:
determining a complex image called the reference complex image by applying a digital reconstruction algorithm to the image acquired by the matrix-array photodetector;
on the basis of said reference complex image, estimating at least one characteristic quantity of the light wave to which the matrix-array photodetector is exposed, at a plurality of reconstruction distances from the latter.

The method may then include:
applying a propagation operator to the reference complex image, so as to calculate what are called secondary complex images for a plurality of distances from the reconstruction plane or from the plane in which the matrix-array photodetector lies; and
determining a characteristic quantity at each of said distances, from each secondary complex image.

The reference complex image may be a complex image formed in a reconstruction plane that is away from the plane of the sample. It may also be a question of a complex image formed in the detection plane.

The method may comprise a step of reconstructing an image of said characteristic quantity in a plane parallel to the detection plane, and at said reconstruction distance, the value of said characteristic quantity at said position of the cell, and at said reconstruction distance, being determined depending on this image.

The position of each cell, in a plane parallel to the detection plane, may be determined using the image acquired by the matrix-array photodetector or using a reconstructed image such as described in the preceding paragraph.

The light source may be a spatially coherent source. It may in particular be a question of a light-emitting diode. The light source may also be temporally coherent; it may in particular be a question of a laser diode.

The matrix-array photodetector or image sensor includes a matrix array of pixels that are able to collect the light wave to which the photodetector is exposed. The distance between the pixels and the sample may vary between 50 μm and 2 cm, and preferably between 100 μm and 5 mm. Preferably the sample is not placed in direct contact with the pixels of the matrix-array photodetector.

Preferably, no magnifying optics are placed between the sample and the matrix-array photodetector.

Another subject of the invention is a device for discriminating a living cell from a dead cell, said cell being placed in a sample, the device comprising:
  a light source that is arranged to produce an incident light wave, along a propagation axis, in the direction of said sample;
  a matrix-array photodetector arranged to acquire an image of the sample, on being exposed to a light wave resulting from interference between said incident light wave and a diffraction wave formed by said cell;
  a holder, for holding the sample between said light source and the matrix-array photodetector;
the device being characterized in that it includes a processor configured to implement the following steps:
  determining a position of said cell in a plane parallel to a detection plane in which the matrix-array photodetector lies;
  applying a digital reconstruction algorithm to said acquired image, so as to determine at least one characteristic quantity of the light wave to which the matrix-array photodetector is exposed, at said position, at a plurality of what are called reconstruction distances from said photodetector along the propagation axis; and
  classifying said cell depending on a profile representing the variation in said characteristic quantity along the propagation axis, this classification being suitable for determining the state of the cell from among preset states.

The processor may be a microprocessor, connected to a programmable memory, including a sequence of instructions for carrying out steps described in this description.

Preferably, the device includes no magnifying optics between the photodetector and the analyzed sample.

The sample may be placed in a transparent chamber, placed between the photodetector and the light source.

Another subject of the invention is an incubator, intended for the growth of cells, comprising a device such as described above.

DISCLOSURE OF PARTICULAR EMBODIMENTS

Figure 1:
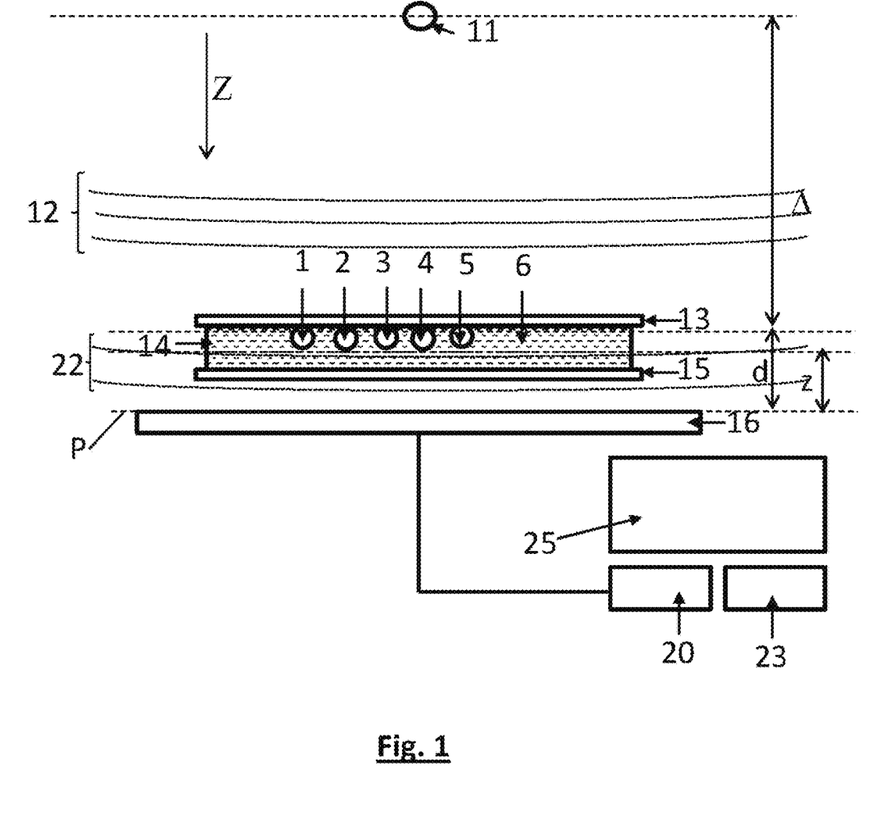
FIG. 1 shows the device according to one embodiment of the invention.

FIG. 1 shows an example of the device that is one subject of the invention. A light source 11 is able to produce a light wave 12, called the incident light wave, in the direction of a sample 14, along a propagation axis Z. The sample 14 includes a culture medium 6 and cells 1, 2, 3, 4, 5 the state of which it is desired to determine—it is in particular desired to determine whether they are alive or dead.

The distance $\Delta$ between the light source and the sample is preferably larger than 1 cm. It is preferably comprised between 2 and 10 cm and is typically 5 cm. Preferably, the light source, seen by the sample, may be considered to be point-like. This means that its diameter (or its diagonal) must be smaller than one fifth and better still one tenth of the distance between the sample and the light source. Thus, the light reaches the sample in the form of plane waves, or waves that may be considered as such.

The light source 11 may be a point source, or be associated with a diaphragm (not shown in FIG. 1) so as to appear point-like. The aperture of the diaphragm is typically comprised between 50 µm and 1 mm and preferably between 50 µm and 500 µm.

The diaphragm may be replaced by an optical fiber, a first end of which is placed facing a light source, and a second end of which is placed facing the sample. In this case, said second end may be likened to a point light source 11.

The sample 14 is bounded by a chamber, including a base 15 and a cover 13. The side walls of the chamber have not been shown. Typically a chamber is a petri dish or a well of a multi-well plate. In the example considered here, the bottom 15 and the cover 13 consist of 2 transparent slides that are a distance of 100 µm apart. The distance d between the cells 1,2,3,4,5 and the photodetector 16 is equal to 3450 µm.

Generally, the thickness of the chamber, along the propagation axis Z, is preferably smaller than a few cm, for example smaller than 5 cm, or even smaller than 1 cm.

The light source 11 may be temporally coherent but this is not necessary.

In this example, the light source is an OSRAM light-emitting diode, of reference LA E67B-U2AA-24-1. It is located a distance Δ equal to 5 cm from the sample.

The sample 14 is placed between the light source 11 and a matrix-array photodetector 16. The latter preferably lies in a detection plane P preferably lying parallelly, or substantially parallelly, to the base 15 of the chamber bounding the sample. The detection plane P preferably lies perpendicularly to the propagation axis Z.

The expression substantially parallelly means that the two elements may not be rigorously parallel, an angular tolerance of a few degrees, smaller than 10°, being acceptable.

Preferably, the light source is of small spectral width, for example of spectral width smaller than 200 nm or even 100 nm or indeed 25 nm. The expression spectral width designates the full width at half maximum of the emission peak of the light source.

The photodetector 16 may be a matrix-array photodetector including a matrix-array of CCD or CMOS pixels. CMOS photodetectors are preferred because the size of the pixels is smaller, this allowing images the spatial resolution of which is more favorable to be acquired. In this example, the detector is a 12-bit APTINA sensor of reference MT9P031. It is a question of an RGB CMOS sensor the inter-pixel pitch of which is 2.2 µm. The useful area of the photodetector is 5.7×4.3 mm². Photodetectors the inter-pixel pitch of which is smaller than 3 µm are preferred, because they allow images with a satisfactory spatial resolution to be obtained.

Preferably, the photodetector comprises a matrix-array of pixels, above which array a transparent protective window is placed. The distance between the matrix-array of pixels and the protective window is generally comprised between a few tens of µm to 150 or 200 µm.

Generally, and whatever the embodiment, the distance d between a particle and the pixels of the photodetector is preferably comprised between 50 µm and 2 cm and preferably comprised between 100 µm and 2 mm.

The absence of magnifying optics between the matrix-array photodetector 16 and the sample 14 will be noted. This does not prevent focusing micro-lenses optionally being present level with each pixel of the photodetector 16.

In this first example, the culture medium is a Dulbecco's Modified Eagle's Medium (DMEM). The sample also contains fibroblast 3T3 cells, the concentration of which is about $0.5 \times 10^6$ cells per ml.

Figure 2:
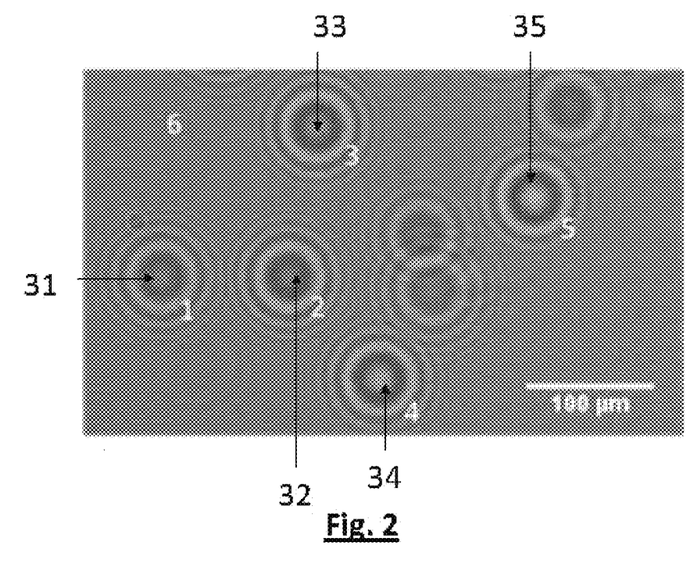
FIG. 2 shows an image acquired by the photodetector in a first example embodiment.

FIG. 2 shows an image obtained by the photodetector 16. This figure shows an overall diffraction pattern, in which elementary diffraction patterns 31, 32, 33, 34, 35, each elementary diffraction pattern being associated with respective cells 1, 2, 3, 4 and 5, may be seen. Each elementary diffraction pattern comprises a central disc-shaped zone, around which alternately dark and light concentric rings extend. The zone referenced by the number 6 corresponds to a background zone including no cell.

Each elementary diffraction pattern (31, . . . 35) is formed by the interference between the incident light wave 12 produced by the source 11, upstream of the sample, and a diffraction wave produced by diffraction of this incident wave by each cell (1, . . . ,5). Thus, the photodetector 16 is exposed to a light wave 22 formed by the superposition:

of the incident light wave 12 emitted by the source 11, upstream of the sample 14; and the diffraction wave produced by each of the cells 1, . . . ,5 or other diffracting elements present in the sample.

A processor 20 receives the images from the matrix-array photodetector 16 and reconstructs characteristic quantities of the light wave 22 to which the photodetector is exposed, along the propagation axis Z. The reconstruction is in particular carried out between the photodetector and the observed sample. The processor 20 may be able to execute a sequence of instructions stored in a memory, in order to implement steps of the identifying method. The microprocessor 20 is connected to a memory 23 able to store instructions for implementing calculating steps described in this application. It may be linked to a screen 25. The processor may be a microprocessor, or any other electronic computer able to process the images delivered by the matrix-array photodetector, in order to execute one or more steps described in this description.

The image shown in FIG. 2 corresponds to the intensity distribution I(x,y), x and y being coordinates in the detection plane P described above.

According to well-known digital holographic reconstruction principles, which are described in the publication by Ryle et al, "Digital in-line holography of biological specimens", Proc. Of SPIE Vol. 6311 (2006), it is possible to reconstruct a complex expression U(x,y,z) for the light wave 22 at any point of spatial coordinates (x,y,z), and in particular in a plane located a distance |z| from the photodetector, and parallel to the plane P in which the photodetector lies, by determining the convolution product of the intensity I(x,y) measured by the photodetector and a propagation operator h(x,y,z).

The function of the propagation operator h(x,y,z) is to describe the propagation of the light between the photodetector 16 and a point of coordinates (x,y,z). It is then possible to determine the amplitude u(x,y,z) and the phase φ (x,y,z) of this light wave 22 at this distance |z|, which is called the reconstruction distance, where:

$$u(x,y,z) = \text{abs}\,[U(x,y,z)]$$

$$\varphi(x,y,z) = \text{arg}\,[U(x,y,z)]$$

The operators abs and arg return the modulus and argument, respectively.

Application of the propagation operator in particular allows the complex expression U(x,y,z) to be estimated at a distance |z| from the photodetector, upstream of the latter. The complex value of the light wave 22 before the latter reaches the detector is thus reconstructed. Back-propagation is then spoken of. If the coordinate z=0 is attributed to the detection plane P, this back-propagation is implemented by applying a propagation operator h(x,y,−|z|).

The terms upstream and downstream are to be understood with respect to the propagation direction of the incident wave 12.

If I(x,y)=I(x,y,z=0) corresponds to the intensity of the signal measured by the photodetector, the relationship between the measured intensity I(x,y) and the complex expression U(x,y) of the light wave, in the detection plane P, is given by: $I(x,y)=|U(x,y)|^2$.

The complex expression of the light wave (22), at a coordinate (x,y,z) is given by $$U(x, y, z) = \sqrt{I(x,y)} * h(x, y, z),$$

the symbol * representing a convolution operator, where:
z<0 in the half-space delineated by the detection plane P and comprising the sample 14; and
z>0 in the half-space delineated by the detection plane P and not comprising the sample 14.

In the half-space delineated by the detection plane P and comprising the sample 14, the complex expression of the light wave may also be written:

$$U(x, y, z) = \sqrt{I(x,y)} * h(x, y, -|z|)$$

Preferably mathematical preprocessing is applied beforehand to the measured intensity I(x,y), before the holographic reconstruction. This allows the quality of the results to be improved, in particular by decreasing the number of artefacts created when the propagation operator is applied.

Thus, an intensity $\bar{I}(x,y)$, called the normalized intensity, is determined, such that $$\bar{I}(x, y) = (I(x, y) - \text{Average }(I))/\text{Average}(I)$$

where
I(x,y)=intensity measured by the photodetector at the coordinate (x,y);
Average (I)=average of the intensity measured in a region of interest of the image I, including said coordinate (x,y). This region of interest may correspond to the entire image formed by the photodetector.

This pre-processing is equivalent to a normalization of the measured intensity by the intensity of the incident light wave 12 the latter being estimated by the quantity Average (I). It allows artefacts generated by the reconstruction process to be limited.

The digital reconstruction may in particular be based on the Fresnel diffraction model. In this example, the propagation operator is the Fresnel-Helmholtz function, such that:

$$h(x, y, z) = \frac{1}{j\lambda z} e^{j2\pi \frac{z}{\lambda}} \exp\left( j\pi \frac{x^2 + y^2}{\lambda z} \right).$$

where λ is the wavelength.
Thus, $$U(x, y, z) = \frac{1}{j\lambda z} e^{j2\pi \frac{z}{\lambda}} \int\int \sqrt{\bar{I}(x', y')} \exp\left( j\pi \frac{(x-x')^2 + (y-y')^2}{\lambda z} \right) dx' dy'$$

where
x' and y' are the coordinates in the plane of the photodetector;
x and y are the coordinates in the reconstruction plane, the latter being located at a distance |z| from the photodetector;
z is the coordinate of the reconstructed image along the propagation axis Z of the incident light wave 12.

From values of the complex expression U(x,y,z), it is possible to extract characteristic quantities of the light wave 22 resulting from the diffraction, by the particles (1,2 . . . 9), of the incident light wave 12 emitted by the source 11. As mentioned above, it is possible to evaluate the amplitude u(x,y,z) or the phase φ(x,y,z), but it is also possible to evaluate any function of the amplitude or phase.

It is for example possible to evaluate a characteristic quantity that is called the complementary amplitude $\tilde{u}(x, y, z)$ such that:

$$\tilde{u}(x, y, z) = \text{abs}(1 - U(x, y, z))$$

From each reconstructed complex expression U(x,y,z), it is possible to form:
an image $u_z$ of the amplitude of the wave 22, in a plane parallel to the plane of the detector, at a distance |z| from the latter, where $u_z(x,y) = \text{abs }[U(x,y,z)]$;
an image $\varphi_z$ of the phase of the wave 22, in a plane parallel to the plane of the detector, at a distance |z| from the latter, where $\varphi_z(x,y) = \text{arg }[U(x,y,z)]$;
an image $\tilde{u}_z$ of the complementary amplitude, such as described above, of the wave 22, in a plane parallel to the plane of the detector, at a distance |z| from the latter, where $\tilde{u}_z(x, y, z) = \text{abs }[1 - U(x,y,z)]$.

Figure 3A:
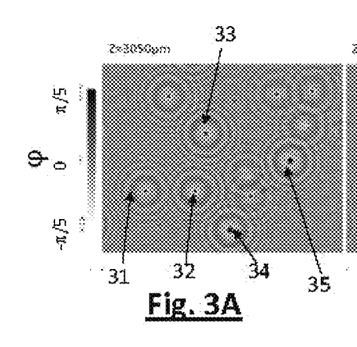
FIGS. 3A to 3C show, for a first example embodiment, images of the phase of the light wave incident on the detector, these images being issued from a holographic reconstruction at three different reconstruction distances.
Figure 3B:
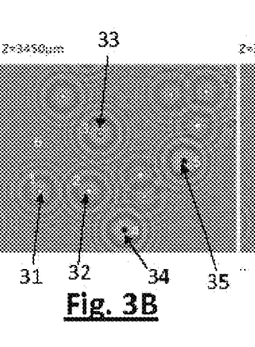
Figure 3C:
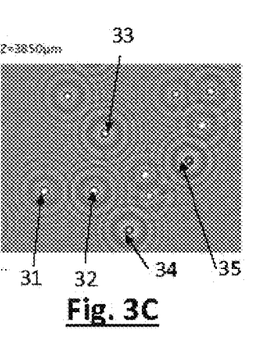

FIGS. 3A to 3C respectively show images $\varphi_z$ of the phase reconstructed in planes parallel to the matrix-array photodetector with |z|=3050 μm, |z|=3450 μm (z=d) and |z|=3850 μm, respectively, the cells being located in the plane |z|=3450 μm.

In each reconstructed image $\varphi_z$ an elementary diffraction pattern (31, 32, 33, 34, 35) corresponding to each cell (1,2,3,4,5) of the sample may be seen, the central portion of each pattern allowing the respective coordinates $(x_1, y_1)$, $(x_2, y_2)$, $(x_3, y_3)$, $(x_4, y_4)$ and $(x_5, y_5)$ of cells 1 to 5 in the detection plane P to be determined. The value of the phase $\varphi(x_1 y_1, z)$, $\varphi(x_2, y_2, z)$, $\varphi(x_3, y_3, z)$, $\varphi(x_4, y_4, z)$, $\varphi(x_5, y_5, z)$ at the various values Z in question is determined:
at |z|=3850 μm, the phase associated with each cell is positive, and of value close to π/5;
at |z|=3450 μm (z=d), the phase associated with cells 1, 2 and 3 is negative (neighboring−π/5), whereas the phase associated with cells 4 and 5 is positive (neighboring+π/5);
at |z|=3050 μm, the phase associated with each cell is negative, and of value close to −π/5.

Thus, in the plane |z|=3450 μm, corresponding to the plane in which the cells are actually located (z=d), the phase of the reconstructed light wave 22 passing through cells 1, 2 and 3, respectively, is negative, whereas the phase of the reconstructed light wave 22 passing through cells 4 and 5, respectively, is negative.

Moreover, following these reconstructions, the cells were treated with Trypan blue, then observed using a microscope at a 10× magnification. Trypan blue is a die commonly used in the field of cell viability. The cells referenced 1, 2 and 3 appeared to be alive, whereas the cells referenced 4 and 5 are dyed blue, indicating a dead cell. These observations serve as reference measurement in the analyses detailed below.

By reconstructing an image of the radiation to which the detector is exposed in the plane containing the cells (z=3450 µm), and by identifying, in this reconstructed image, the position of each cell, it is possible to discriminate living cells (negative phase) from dead cells (positive phase).

Figure 4A:
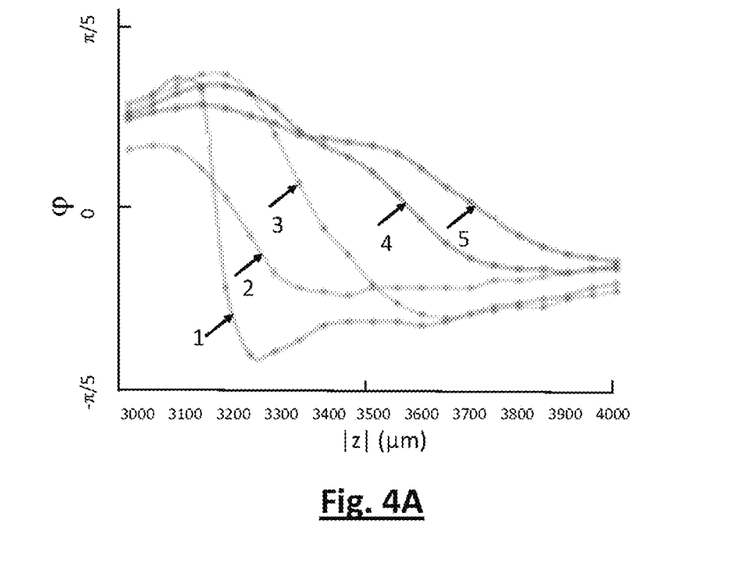
FIGS. 4A and 4B respectively show, for a first example embodiment, the profile of the phase and the profile of another characteristic quantity, called the complementary amplitude, along the propagation axis, for 5 cells.

FIG. 4A illustrates, for each cell n (1≤n≤5), the variation in the profile $\varphi(x_n, y_n, z)$ of the phase as a function of z, for |z| comprised between 3000 µm and 4000 µm. The profiles corresponding to living cells (n=1, 2 and 3) are characterized by a marked slope at |z|<3450 µm, whereas the profiles corresponding to the dead cells (n=4 or 5) are characterized by a gradual decrease in the phase along the propagation axis Z, in the direction pointing from the matrix-array photodetector to the sample.

Thus, it is possible to establish a profile representing the variation in the phase of the wave 22 to which the detector is exposed along an axis, parallel to the propagation axis Z, passing through each cell. This profile may then be used to perform a classification between a living cell and a dead cell. This profile may in particular be compared to a library of profiles produced with "standard" cells the state of which is known. In other words, the profile representing the variation in the phase along the propagation axis of the light wave forms a signature of the state of the cell.

Reconstructing a characteristic quantity of the wave 22 resulting from diffraction by a particle and the incident wave 12 not at a single reconstruction distance, but along the propagation axis of the incident wave, at a plurality of reconstruction distances, allows richer information to be obtained. This allows the various states of a cell to be reliably classified. Moreover, this makes it possible to avoid needing to know the precise distance separating a cell to be characterized from the photodetector.

Another indicator may be the distance $|z_0|$ at which the phase value $\varphi(x_n, y_n, z)$ passes through zero, a cell being considered to be alive if $|z_0|$ is lower than the distance d actually separating the cell from the photodetector (in the present case d=3450 µm), and dead in the contrary case.

Figure 4B:
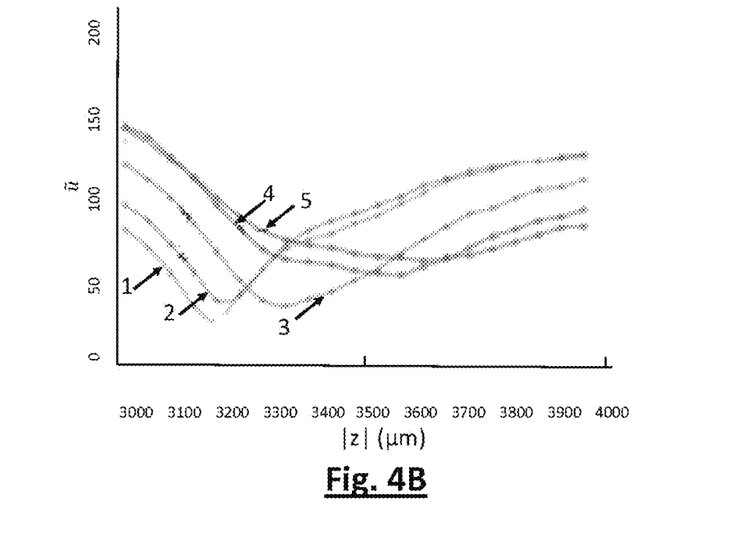

FIG. 4B shows, for each cell n (1≤n≤5), the variation in the profile $\tilde{u}(x_n, y_n, z)$ of the complementary amplitude as a function of z, for |z| comprised between 3000 µm and 4000 µm. The profiles corresponding to living cells (n=1, 2 and 3) are characterized by a minimum value $\tilde{u}_{min} \leq 50$, whereas for dead cells the minimum value $\tilde{u}_{min}$ of the profile is higher than 50. In other words, it is possible to define a threshold value $\tilde{u}_{threshold}$, comparison of this threshold value $\tilde{u}_{threshold}$ with a noteworthy point of the profile, in the present case the minimum value, allowing the cell to be classed as alive or dead.

From FIG. 4B it will also be noted that when the cells are alive, the minimum value $\tilde{u}_{min}$ of the profile is reached at |z|<3450 µm, this not being the case for dead cells. In other words, it is possible to identify the position $z_{min}$, along the propagation axis Z, of a noteworthy point of the profile, in the present case a minimum, and to compare this position to the distance d between the analyzed cell and the photodetector. If $|z_{min}| \leq d$, the cell is considered to be viable. Otherwise, it is considered to be dead.

It is therefore possible to establish a profile representing the variation in the complementary amplitude $\tilde{u}$ of the light wave 22 to which the detector is exposed, along the propagation axis Z and passing through each cell, and to use this profile to perform a classification between a living cell and a dead cell. This profile may in particular be compared to a library of profiles produced with "standard" cells the state of which is known. In other words, the profile representing the variation in the complementary amplitude $\tilde{u}$ along the propagation axis forms a signature of the state of the cell.

In a second example, the device is similar to that implemented above. The characterized cells are PC12 cells. Just as in the first example above, an image was acquired on the matrix-array photodetector, in an identical configuration to the configuration shown in FIG. 1. This image allowed a complex expression U(x,y,z) of the wave 22 to which the photodetector was exposed to be reconstructed, along the propagation axis Z, the reconstruction distance varying from 3000 µm to 3800 µm.

A reference measurement was then carried out, using staining with Trypan blue, allowing dead cells D and living cells A to be identified.

Figure 5A:
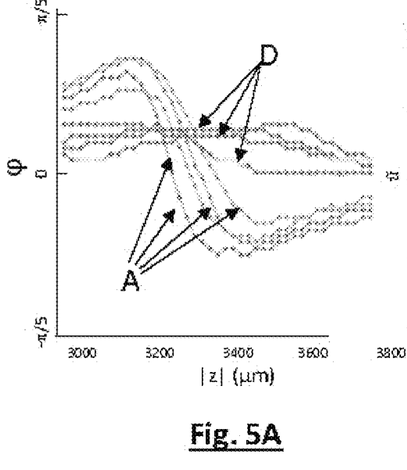
FIGS. 5A and 5B respectively show, for a second example embodiment, the profile of the phase and the profile of another characteristic quantity, called the complementary amplitude, along the propagation axis, for a plurality of cells.

FIG. 5A shows the variation in the phase $\varphi(x_n, y_n, z)$ as a function of |z|, $(x_n, y_n)$ being the coordinates of the center of each examined cell n. Just as in the preceding example, it is observed that:
the phase $\varphi(x_n, y_n, |z|=d=3450$ µm) is negative for living cells, and positive or zero for dead cells;
the profile $\varphi(x_n, y_n, z)$ associated with each living cell is characterized by a marked decrease in the phase at |z|<d, whereas the profile $\varphi(x_n, y_n, z)$ associated with each dead cell is characterized by a slower variation in the profile as a function of z. The profile representing the variation in the phase along the propagation axis Z therefore forms a signature of the state of the cell; and
the value $|z_0|$ at which the phase of the reconstructed wave 22 is equal to 0 varies depending on the state of the cells: $|z_0|<d$ for living cells and $|z_0| \leq d$ for dead cells.

Thus there are 3 criteria for classifying a cell: value of the phase at |z|=d, variation in the phase as a function of z and the value $|z_0|$ at which the value of the phase of the complex expression of the reconstructed wave 22 is zero.

Figure 5B:
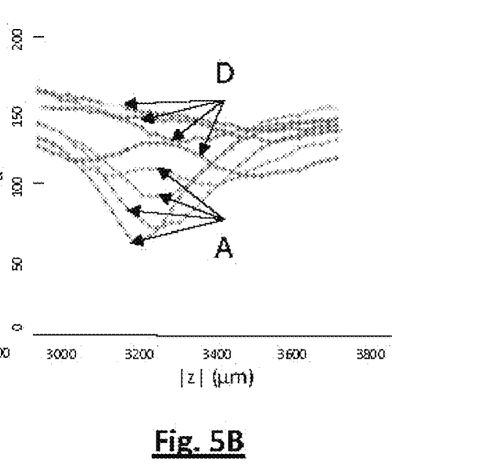

FIG. 5B shows the variation in the complementary amplitude $\tilde{u}$ $(x_n, y_n, z)$ such as defined above as a function of z, $(x_n, y_n)$ being the coordinates of the center of each examined cell n. Just as in the preceding example, the variation in the profile of the complementary amplitude is different depending on whether the cell is alive or dead. In particular, when the minimum value $\tilde{u}_{min}$ of the profile is lower than a threshold value $\tilde{u}_{threshold}$, here of about 100, a cell is declared to be alive, and dead in the contrary case In a third example, the device is similar to that implemented above. The characterized cells are CHO cells (CHO standing for Chinese hamster ovary—cell line derived from the ovary of the Chinese hamster). Just as in the two examples above, an image is acquired on the matrix-array photodetector, in an identical configuration to the configuration shown in FIG. 1. This image allowed a complex expression U(x,y,z) of the wave 22 to which the photodetector is exposed to be reconstructed, along the propagation axis Z, the reconstruction distance |z| varying from 3000 µm to 3800 µm.

A reference measurement was then carried out, using staining with Trypan blue, allowing dead cells D and living cells A to be identified.

Figure 6A:
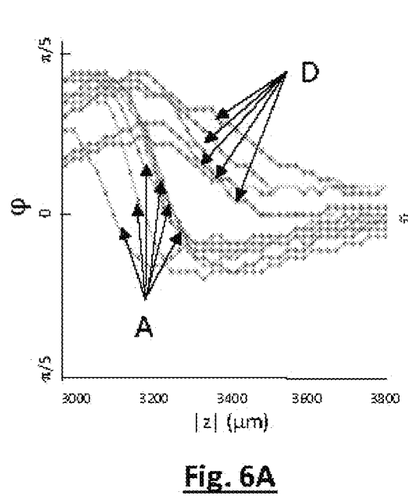
FIGS. 6A and 6B respectively show, for a third example embodiment, the profile of the phase and the profile of another characteristic quantity, called the complementary amplitude, along the propagation axis, for a plurality of cells.

FIG. 6A shows the variation in the phase $\varphi(x_n, y_n, z)$ as a function of z, $(x_n, y_n)$ being the coordinates of the center of each characterized cell n. Just as in the preceding example, it is observed that:
the phase $\varphi(x_n, y_n, |z|=d=3450$ µm) is negative for living cells, and positive for dead cells;
the profile $\varphi(x_n, y_n, z)$ associated with each living cell is characterized by a marked decrease in the phase at |z|<d, whereas the profile $\varphi(x_n, y_n, z)$ associated with each dead cell is characterized by a slower variation in the profile as a function of z. The profile representing the variation in the phase along the propagation axis Z therefore forms a signature of the state of the cell; and the value $|z_0|$ at which the phase of the wave 22 is equal to 0 varies depending on the state of the cells: $|z_0|<d$ for living cells and $|z_0|>d$ for dead cells.

Figure 6B:
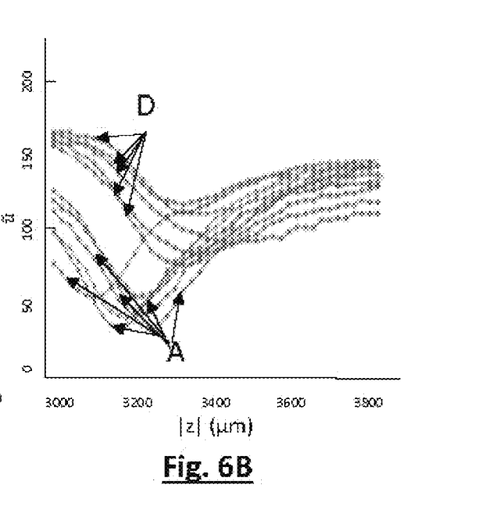

FIG. 6B shows the variation in the complementary amplitude $\tilde{u}$ ($x_n$, $y_n$, z) such as defined above as a function of z, ($x_n$,$y_n$) being the coordinates of the center of each examined cell n. Just as in the preceding example, the variation in the profile of the complementary amplitude is different depending on whether the cell is alive or dead. In particular, when the minimum value $\tilde{u}_{min}$ of the profile is lower than a threshold value $\tilde{u}_{threshold}$, here equal to 30, a cell is declared to be alive, or dead in the contrary case.

According to one variant, the classification between a living cell and a dead cell is achieved by combining, for a given height z, various parameters of the light radiation 22 to which the detector is exposed. According to one example, the phase $\varphi(x,y,z)$ and the complementary amplitude $\tilde{u}$(x,y,z) are determined along the propagation axis Z, the classification being achieved using the ratio of these two parameters.

Figure 7:
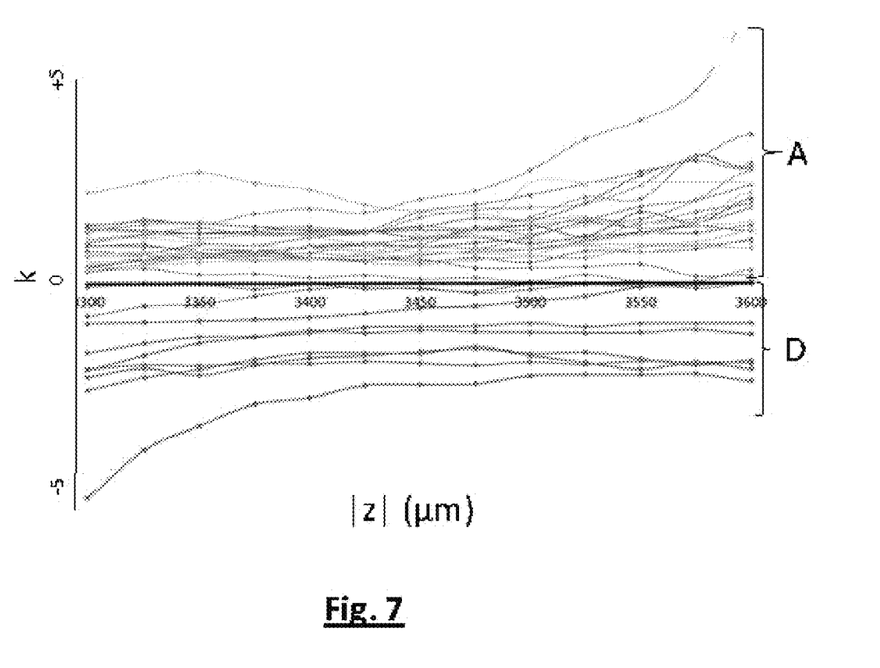
FIG. 7 shows, in relation with this third example embodiment, the profile of a composite quantity combining the phase and absorption along the propagation axis for a plurality of cells.

FIG. 7 shows the profile, along the propagation axis Z, of the composite quantity k(x,y,z) such that $$k(x, y, z) = \frac{\varphi(x, y, z)}{\tilde{u}(x, y, z)} - k(x_6, y_6, z),$$

the term $k(x_6, y_6, z)$ representing the ratio $$\frac{\varphi(x, y, z)}{\tilde{u}(x, y, z)}$$

determined in a portion 6 of the sample exempt of cells. This ratio may be called the reference ratio.

This figure shows the variation in the composite quantity $k(x_n,y_n,z)$ for n cells, each cell n being identified by its position in the plane ($x_n$,$y_n$) of the photodetector.

The value of the composite quantity, at a given reconstruction distance z, is systematically higher for living cells than for dead cells. It is thus possible to define a threshold $k_{threshold}(z)$, such that if $k(x_n,y_n, z) \geq k_{threshold}(z)$, the cell centered on the position ($x_n$,$y_n$), in the plane P, is alive, or dead in the contrary case.

Figures 8A, 8B, 8C, 8D, 8E, 8F:
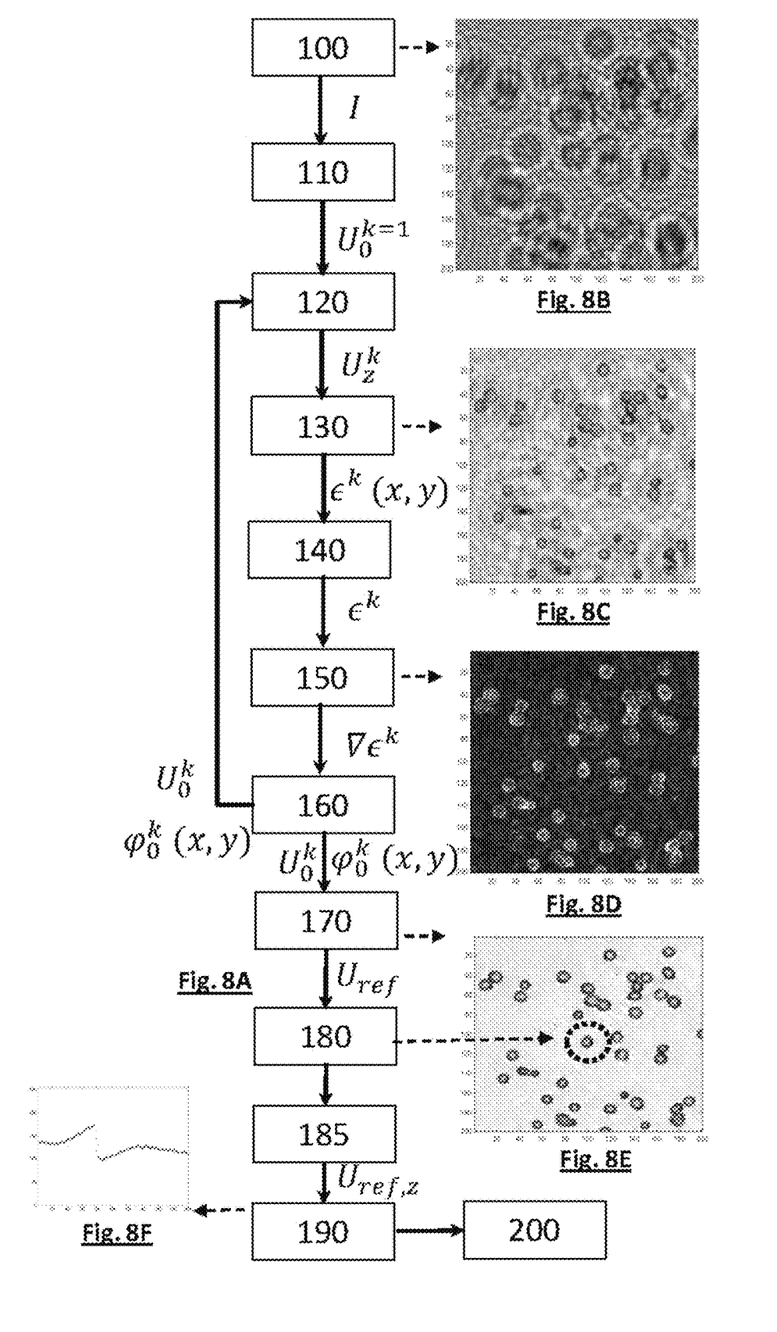
FIG. 8A illustrates the main steps of a method allowing a complex image of a sample to be calculated in a reconstruction plane.
FIGS. 8B, 8C, 8D, 8E and 8F respectively show:
  an image acquired by the matrix-array photodetector, this image also being referred to as a "hologram";
  an image reconstructed in a reconstruction plane in a first iteration of the method shown in FIG. 8A;
  an image showing a quantity associated with each pixel of the image shown in FIG. 8C;
  a representation of an image, called a reference complex image, reconstructed after a plurality of iterations of the method shown in FIG. 8A; and
  a profile obtained on the basis of secondary complex images formed from the reference complex image.

Application of a digital propagation operator h to an image I, or hologram, acquired by a matrix-array photodetector 16 may have certain limits, because the acquired image includes no phase-related information. Thus, before the profile is established, it is preferable to obtain information relating to the phase of the light wave 22 to which the photodetector 16 is exposed. This phase-related information may be obtained by reconstructing a complex image $U_z$ of the sample 14, using methods described in the prior art, so as to obtain an estimation of the amplitude and phase of the light wave 22 in the plane P of the matrix-array photodetector 16 or in a reconstruction plane $P_z$ located at a distance |z| from the latter. The inventors have developed a method based on the calculation of a reference complex image, which method is described with reference to FIG. 8A. This method comprises the following steps:

Acquiring an image I of the sample 14 with the matrix-array photodetector 16, this image forming the hologram (step 100).

Calculating a complex image called the reference image $U_{ref}$ of the sample 14 in a reconstruction plane $P_z$ or in the detection plane P, this reference complex image including information on the phase and amplitude of the light wave 22 to which the matrix-array photodetector 16 is exposed; this step is carried out by applying the propagation operator h described above to the acquired image I (steps 110 to 170). This complex image is said to be a reference image because the formation of the profile on the basis of which the particle is characterized is based thereon.

Selecting a radial position (x,y) of a particle in the detection plane or in a plane parallel to the latter (step 180), either using the reference complex image $U_{ref}$ or the image I acquired by the photodetector 16.

Applying the propagation operator it to the reference complex image $U_{ref}$ so as to calculate complex images $U_{ref,z'}$ called secondary images, along the propagation axis Z (step 185).

On the basis of each secondary complex image $U_{ref,z'}$, estimating a characteristic quantity of the light wave 22, at the radial position (x,y) of the particle selected beforehand, and at a plurality of distances from the reconstruction plane $P_z$ (or from the detection plane P), and then forming a profile representing a variation in said characteristic quantity along the propagation axis Z (step 190).

Characterizing the particle depending on said profile. As indicated above, this characterization may be achieved by comparing the obtained profile with standard profiles obtained in a calibrating phase, using standard samples (step 200).

The algorithm presented in FIG. 8A is detailed below, the results obtained in certain steps being illustrated in FIGS. 8B to 8F. Steps 110 to 170 are a preferred way of obtaining a reference complex image, denoted $U_{ref}$, this image representing a spatial distribution of the complex expression of the wave 22 in a reconstruction plane $P_z$. Those skilled in the art will understand that other algorithms allow such a complex image to be reconstructed, it for example also being envisionable to use the algorithms mentioned with reference to the prior art.

Step 100: Image Acquisition

In this step, the image sensor 16 acquires an image I of the sample 14, and more precisely of the light wave 22 transmitted by the latter, to which light wave the image sensor is exposed. Such an image, or hologram, is shown in FIG. 8B.

This image was produced using a sample 10 including Chinese hamster ovary (CHO) cells immersed in a saline buffer, the sample being contained in a fluidic chamber of 100 µm thickness placed at a distance d of 1500 µm from a CMOS sensor. The sample was illuminated with a light-emitting diode 11 the spectral emission band of which was centered on a wavelength of 450 nm and which was located at a distance D=8 cm from the sample.

Step 110: Initialization

In this step, an initial image $U_0^{k=0}$ of the sample 14 is defined, from the image I acquired by the image sensor 16. This step is an initialization of the iterative algorithm described below with regard to steps 120 to 180, the exponent k indicating the rank of each iteration. The modulus $u_0^{k=0}$ of the initial image $U_0^{k=0}$ may be obtained by applying the square-root operator to the image I acquired by the image sensor, in which case $u_0^{k=0}=\sqrt{I_0}$.

The phase $\varphi_0^{k=0}$ of the initial image $U_0^{k=0}$ is either considered to be zero in each pixel (x,y), or preset to an arbitrary value. Specifically, the initial image $U_0^{k=0}$ results directly from the image I acquired by the matrix-array photodetector 16. However, the latter includes no information relating to the phase of the light wave 22 transmitted by the sample 14, the image sensor 16 being sensitive only to the intensity of this light wave.

Step 120: Propagation

In this step, the image $U_0^{k-1}$ obtained in the plane of the sample is propagated to a reconstruction plane $P_z$, by applying a propagation operator such as described above, so as to obtain a complex image $U_z^k$, representative of the sample 14, in the reconstruction plane $P_z$. The propagation is carried out by convoluting the image $U_0^{k-1}$ with the propagation operator $h_{-z'}$ such that:

$$U_z^k = U_0^{k-1} * h_{-z'}$$

the symbol * representing a convolution operator. The index −z represents the fact that the propagation is carried out in a direction opposite to that of the propagation axis Z. Back-propagation is spoken of.

In the first iteration (k=1), $U_0^{k=0}$ is the initial image determined in step 110. In the following iterations, $U_0^{k-1}$ is the complex image in the detection plane P updated in the preceding iteration.

The reconstruction plane $P_z$ is a plane away from the detection plane P, and preferably parallel to the latter. Preferably, the reconstruction plane $P_z$ is a plane $P_{14}$ in which the sample 14 lies. Specifically, an image reconstructed in this plane allows a generally high spatial resolution to be obtained. It may also be a question of another plane, located a nonzero distance from the detection plane, and preferably parallel to the latter, for example a plane lying between the matrix-array photodetector 16 and the sample 14.

FIG. 8C shows the modulus of an image $U_z^{k=1}$ reconstructed at a distance of 1440 μm from the detection plane P by applying the propagation operator defined above to the hologram of FIG. 8B. This image is the complex image, in the reconstruction plane, established in the first iteration.

Step 130: Calculation of an Indicator in a Plurality of Pixels

In this step, a quantity $\varepsilon^k(x,y)$ associated with each pixel of a plurality of pixels (x,y) of the complex image $U_z^k$ is calculated, preferably in each of these pixels. This quantity depends on the value $U_z^k(x,y)$ of the image $U_z^k$, or of its modulus, in the pixel (x,y) for which it is calculated. It may also depend on a dimensional derivative of the image in this pixel, for example the modulus of a dimensional derivative of this image.

In this example, the quantity associated with each pixel (x,y) is based on the modulus of a dimensional derivative, such that:

$$\varepsilon^k(x, y) = \sqrt{\left|\frac{\partial U_z^k(x, y)}{\partial x}\right|^2 + \left|\frac{\partial U_z^k(x, y)}{\partial y}\right|^2}.$$

Since the image is discretized into pixels, the derivative operators may be replaced by Sobel operators, such that:

$$\varepsilon^k(x, y) = \sqrt{(S_x * U_z^k(x, y))(S_x * U_z^k(x, y))^* + (S_y * U_z^k(x, y))(S_y * U_z^k(x, y))^*}$$

where:

( )* is the complex conjugate operator; and $S_x$ and $S_y$ are Sobel operators along two orthogonal axes X and Y of the reconstruction plane $P_z$.

In this example, $$S_x = \begin{bmatrix} 1 & 0 & -1 \\ 2 & 0 & -2 \\ 1 & 0 & -1 \end{bmatrix}$$

and $S_y$ is the transposed matrix of $S_x$.

FIG. 8D shows, in the form of an image, the value of the modulus $\varepsilon^k(x,y)$ in each pixel of the image $A_z^{k=1}$ shown in FIG. 8C.

Step 140: Establishment of a Noise Indicator Associated with the Image $U_z^k$ In step 130, quantities $\varepsilon^k(x,y)$ were calculated in a plurality of pixels of the complex image $U_z^k$. These quantities may form a vector $E^k$, the terms of which are the quantities $\varepsilon^k(x,y)$ associated with each pixel (x,y). In this step, an indicator, called the noise indicator, is calculated from a norm of the vector $E^k$. Generally, an order is associated with a norm, such that the norm $\|x\|_p$ of order p of a vector x of dimension n of coordinates $(x_1, x_2, \ldots x_n)$ is such that: $\|x\|_p = (\Sigma_{i=1}^n |x_i|^p)^{1/p}$, where $p \geq 0$.

In the present case, a norm of order 1 is used, in other words p=1. Specifically, the inventors have estimated that a norm of order 1, or of order lower than or equal to 1, is particularly suitable for such a sample, as explained below.

In this step, the quantity $\varepsilon^k(x,y)$ calculated from the complex image $U_z^k$, in each pixel (x,y) of the latter, is summed so as to form a noise indicator $\varepsilon^k$ associated with the complex image $U_z^k$.

Thus, $$\varepsilon^k = \Sigma_{(x,y)} \varepsilon^k(x, y)$$

This noise indicator $\varepsilon^k$ corresponds to a norm of the total variation in the complex image $A_z^k$.

With reference to the example of FIG. 8D, the noise indicator $\varepsilon^{k=1}$ is obtained, in the first iteration, by summing the value of the pixels of this image.

Because a norm of order 1, or of order lower than or equal to 1, is used, the value of the noise indicator $\varepsilon^k$ decreases as the complex image $U_z^k$ becomes more and more representative of the sample. Specifically, in the first iterations, the value of the phase $\varphi_0^k(x,y)$, in each pixel (x,y) of the image $U_0^k$ is poorly estimated. Propagation of the image of the sample from the detection plane P to the reconstruction plane $P_z$ is then accompanied by substantial reconstruction noise, as mentioned with regard to the prior art. This reconstruction noise takes the form of fluctuations in the reconstructed image. Because of these fluctuations, a noise indicator $\varepsilon^k$, such as defined above, increases in value as the contribution of the reconstruction noise, in the reconstructed image, increases. Specifically, the fluctuations due to the reconstruction noise tend to increase the value of this indicator.

An important aspect of this step consists in determining, in the detection plane P, phase values $\varphi_0^k(x,y)$ for each pixel of the image of the sample $U_0^k$, this allowing, in a following iteration, a reconstructed image $U_z^{k+1}$ to be obtained the indicator of which $\varepsilon^{k+1}$ is lower than the indicator $\varepsilon^k$.

In the first iteration, as explained above, relevant information is available only on the intensity of the light wave 22 and not on its phase. The first image $U_z^{k=1}$ reconstructed in the reconstruction plane $P_z$ is therefore affected by a substantial amount of reconstruction noise, because of the absence of relevant information as to the phase of the light wave 22 in the detection plane P. Therefore, the indicator $\varepsilon^{k=1}$ is high. In following iterations, the algorithm carries out a gradual adjustment of the phase $\varphi_0^k(x,y)$ in the detection plane P, so as to gradually minimize the indicator $\varepsilon^k$.

The image $U_0^k$ in the detection plane is representative of the light wave 22 in the detection plane P, both from the point of view of its intensity and of its phase. Steps 120 to 160 aim to establish, iteratively, for each pixel of the image $U_0^k$, the value of the phase $\varphi_0^k(x,y)$ which minimizes the indicator $\varepsilon^k$, the latter being obtained from the image $U_z^k$ obtained by propagating the image $U_0^{k-1}$ to the reconstruction plane $P_z$.

The minimization algorithm may be a gradient descent algorithm, or a conjugated gradient descent algorithm, the latter being described below.

Step 150: Adjustment of the value of the phase in the detection plane.

Step 150 aims to determine a value of the phase $\varphi_0^k(x,y)$ of each pixel of the complex image $U_0^k$, so as to minimize, in the following iteration k+1, the indicator $\varepsilon^{k+1}$ resulting from a propagation of the complex image $U_0^k$ to the reconstruction plane $P_z$. To do this, a phase vector $\varphi_0^k$ is established, each term of which is the phase $\varphi_0^k(x,y)$ of a pixel (x,y) of the complex image $U_0^k$. The dimension of this vector is $(N_{pix}, 1)$, where $N_{pix}$ is the number of pixels in question. This vector is updated in each iteration, using the following updating expression:

$$\varphi_0^k(x,y) = \varphi_0^{k-1}(x,y) + \alpha^k p^k(x,y)$$

where:
- $\alpha^k$ is an integer, called the "step size", representing a distance;
- $p^k$ is a direction vector, of dimension $(N_{pix}, 1)$, each term $p(x,y)$ of which forms a direction of the gradient $\nabla \varepsilon^k$ of the indicator $\varepsilon^k$.

This equation may be expressed in vectorial form as follows:

$$\varphi_0^k = \varphi_0^{k-1} + \alpha^k p^k$$

It may be shown that:

$$p^k = -\nabla \varepsilon^k + \beta^k p^{k-1}$$

where:
- $\nabla \varepsilon^k$ is a gradient vector, of dimension $(N_{pix}, 1)$, each term of which represents a variation in the indicator $\varepsilon^k$ as a function of each of the degrees of freedom of the unknowns of the problem, i.e. the terms of the vector $\varphi_0^k$;
- $p^{k-1}$ is a direction vector established in the preceding iteration;
- $\beta^k$ is a scale factor applied to the direction vector $p^{k-1}$.

Each term $\nabla \varepsilon^k(x,y)$ of the gradient vector $\nabla \varepsilon$ is such that $$\nabla \varepsilon^k(r') = \frac{\partial \varepsilon^k}{\partial \varphi_0^k(r')} = -\text{Im}\left(U_0^{k*}(r')\left(\left(S_x * \frac{S_x * U_z^k}{\varepsilon^k} + S_y * \frac{S_y * U_z^k}{\varepsilon^k}\right) \cdot * h_z\right)(r')\right)$$

where Im is an operator returning the imaginary part of the operand and r' is a coordinate (x,y) in the detection plane.

The scale factor $\beta^k$ may be expressed such that:

$$\beta^{(k)} = \frac{\nabla \varepsilon^{(k)} \cdot \nabla \varepsilon^{(k)}}{\nabla \varepsilon^{(k-1)} \cdot \nabla \varepsilon^{(k-1)}}$$

The step size $\alpha^k$ may vary depending on the iteration, for example from 0.03 in the first iterations to 0.0005 in the last iterations.

The updating equation allows an adjustment of the vector $\varphi_0^k$ to be obtained, this leading to an iterative update of the phase $\varphi_0^k(x,y)$ in each pixel of the complex image $U_0^k$. This complex image $U_0^k$, in the detection plane, is then updated with these new values of the phase associated with each pixel. It will be noted that the modulus of the complex image $U_0^k$ is not modified, the latter being determined from the image acquired by the matrix-array photodetector 16, such that $u_0^k(x,y) = u_0^k(x,y)$.

Step 160: Reiteration of or exit from the algorithm.

Provided that a convergence criterion has not been reached, step 160 consists in reiterating the algorithm, with a new iteration of steps 120 to 160, on the basis of the complex image $U_0^k$ updated in step 150. The convergence criterion may be a preset number K of iterations, or a minimum value of the gradient $\nabla \varepsilon^k$ of the indicator, or a difference considered to be negligible between two consecutive phase vectors $\varphi_0^{k-1}, \varphi_0^k$. When the convergence criterion is reached, the estimation is considered to be a correct estimation of a complex image of the sample, in the detection plane P or in the reconstruction plane $P_z$.

Step 170: Obtainment of the reference complex image.

At the end of the last iteration, the method may comprise propagating the complex image $U_0^k$ resulting from the last iteration to the reconstruction plane $P_z$, so as to obtain a reference complex image $U_{ref} = U_z^k$. Alternatively, the reference complex image $U_{ref}$ is the complex image $U_0^k$ resulting from the last iteration in the detection plane P. When the density of the particles is high, this alternative is however less advantageous because the spatial resolution in the detection plane P is lower than in the reconstruction plane $P_z$, in particular when the reconstruction plane $P_z$ corresponds to a plane $P_{14}$ in which the sample 14 lies.

FIG. 8E shows an image of the modulus $u_z^{k=30}$ of each pixel of the reference complex image $U_z^{k=30}$ obtained in a reconstruction plane $P_z$ after 30 iterations. This image may be compared to FIG. 8C, showing a similar image $A_z^{k=1}$ obtained in the first iteration. A clear decrease in reconstruction noise is observed, in particular between each pixel. Moreover, the spatial resolution of this image allows a good identification of the radial coordinates (x,y) of each particle.

Step 180: Selection of particle radial coordinates.

In this step, the radial coordinates (x,y) of a particle are selected from the reference image $U_{ref} = U_z^{k=30}$, for example from the image of its modulus $u_{ref} = u_z^{k=30}$ or the image of its phase $\varphi_{ref} = \varphi_z^{k=30}$. As mentioned above, the expression radial coordinate designates a coordinate in the detection plane or in the reconstruction plane. It is also envisionable to carry out this selection on the basis of the hologram $I_0$ or of the complex image $U_0^k$ obtained in the detection plane following the last iteration. However, when the number of particles increases, it is preferable to carry out this selection on the image formed in the reconstruction plane, because of its better spatial resolution, in particular when the reconstruction plane $P_z$ corresponds to the plane of the sample $P_{14}$. In FIG. 8E, the selection of a particle, which is encircled by a dotted outline, has been shown.

Step 185: Application of a Propagation Operator

In this step 185, the reference complex image $U_{ref}$ is propagated to a plurality of reconstruction distances, using a propagation operator h such as defined above, so as to obtain a plurality of what are called secondary complex images $U_{ref,z}$ reconstructed at various distances from the detection plane P or from the reconstruction plane $P_z$. Thus, this step comprises determining a plurality of complex images $U_{ref,z}$ such that:

$$U_{ref,z} = U_{ref} * h_z \text{ with } z_{min} \leq z \leq z_{max}.$$

The values $z_{min}$ and $z_{max}$ the minimum and maximum coordinates, along the axis Z, to which the reference complex image is propagated. Preferably, the complex images are reconstructed at a plurality of coordinates z between the sample 14 and the image sensor 16. The complex images may be formed on either side of the sample 14.

These secondary complex images are established by applying a holographic reconstruction operator h to the reference image $U_{ref}$. The latter is a complex image correctly describing the light wave 22 to which the image sensor is exposed, and in particular its phase, following the iterations of the steps 120 to 160. Therefore, the secondary images $U_{ref,z}$ form a good descriptor of the propagation of the light wave 22 along the propagation axis Z.

Step 190: Formation of a Profile

In this step, from each secondary complex image $U_{ref,z}$, a characteristic quantity, such as defined above, of the light wave 22 is determined so as to define a profile representing the variation in said characteristic quantity along the propagation axis Z. The characteristic quantity may, for example, be the modulus or the phase, or a combination thereof. FIG. 8F shows the variation in the phase $\varphi(z)$ of the light wave 22 along the propagation axis Z.

Step 200: Characterization

The particle may then be characterized from the profile formed in the preceding step. Preferably, there is available a database of standard profiles formed in a learning phase using known standard samples. The characterization is then carried out by comparing or classifying the formed profile on the basis of the standard profiles.

This embodiment, which is based on formation of a reference complex image, was implemented, using the norm of the total variation, on CHO (Chinese hamster ovary) cells immersed in a CD CHO culture medium (Thermo Fisher). The sample was placed in a fluidic chamber of 100 µm thickness and positioned at a distance of 8 cm from a light-emitting diode, the spectral band of which was centered on 450 nm. The sample was placed at a distance of 1500 µm from a CMOS image sensor of 2748×3840 pixels. The aperture of the spatial filter 18 had a diameter of 150 µm.

Figure 9A:
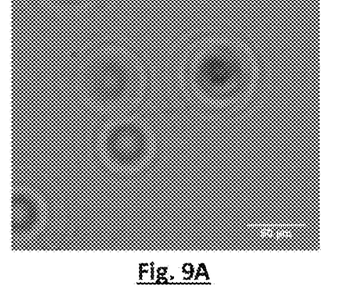
FIG. 9A is a hologram acquired by an image sensor, the sample including cells dispersed in an aqueous solution.
Figure 9B:
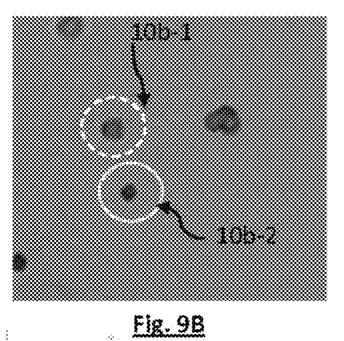
FIGS. 9B and 9C respectively show the modulus and phase of a complex image that is what is called a reference image, this complex image being formed in a reconstruction plane.
Figure 9C:
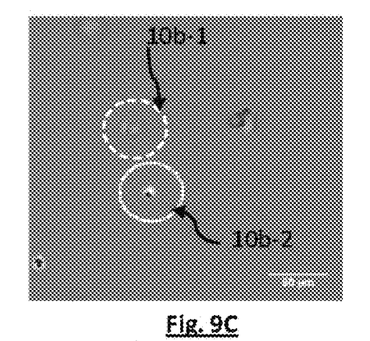

FIG. 9A shows an image I acquired by the matrix-array photodetector 16. The images of the modulus and of the phase of the reference complex image $U_z^k$ reconstructed, in the plane $P_{14}$ of the sample, are shown in FIGS. 5B and 5C, respectively. These images were obtained in 100 iterations. The uniformity of the gray-scale representation of each cell attests to the quality of the reconstruction. A propagation operator h such as described above was applied to this reference image in order to obtain a plurality of secondary complex images $U_{ref,z}$ along the propagation axis Z. Moreover, in the image of the modulus or in the image of the phase of the reference image, two cells were identified, respectively encircled by a black dashed outline (cell 10b-1) and a black dotted outline (cell 10b-2) in FIGS. 9B and 9C. The radial coordinates (x,y) of these two cells were extracted. For each cell, a profile u(z) representative of the modulus and a profile $\varphi(z)$ representative of the phase of the light wave 22 reaching the image sensor 16 were formed. The value of each point of the profile is obtained by determining the modulus and phase of a respective secondary complex image $U_{ref,z}$ at said radial coordinates (x,y).

Figure 9D:
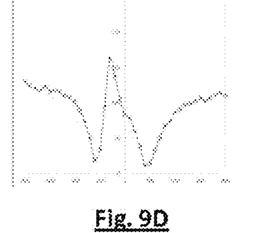
FIGS. 9D and 9E are profiles respectively showing a variation in the modulus and phase of the light wave to which the image sensor is exposed, along a propagation axis passing through a first cell.
Figure 9E:
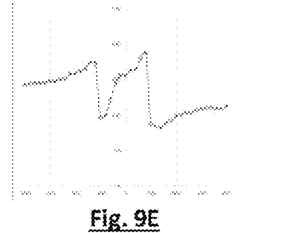
Figure 9F:
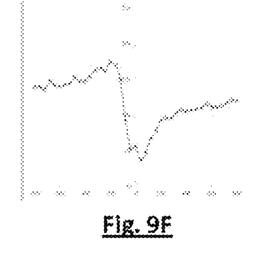
FIGS. 9F and 9G are profiles respectively showing a variation in the modulus and phase of the light wave to which the image sensor is exposed, along a propagation axis passing through a second cell.
Figure 9G:
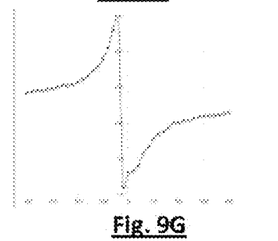

FIGS. 9D and 9E respectively show the profile of the modulus and of the phase of the cell 10b-1. FIGS. 9F and 9G respectively show the profile of the modulus and of the phase of the cell 10b-2.

Figure 9H:
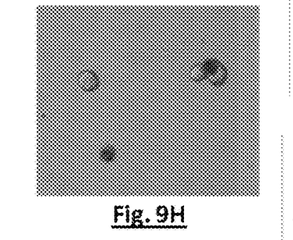
FIG. 9H is a microscope image of the observed sample.

Moreover, following these reconstructions, the cells were treated with Trypan blue, then observed using a microscope at a 10× magnification. The image obtained is shown in FIG. 9H. The cell 10b-1 is a living cell, whereas the cell 10b-2 appears to be a dead cell.

The profiles of modulus or phase of FIGS. 9D and 9E may be considered to be representative of a living CHO cell, whereas FIGS. 9F and 9G may be considered to be representative of a dead CHO cell. CHO cells may be characterized on the basis of such profiles.

The examples described above provide simple identification criteria based on the variation in the profile of a characteristic quantity as a function of reconstruction distance, and on comparisons using preset thresholds. In addition, other classifying methods that are more complex and more robust may be implemented, without departing from the scope of the invention.

The invention claimed is:

1. A method for determining a state of a cell, the cell being placed in a sample, the method comprising:
   illuminating the sample using a light source, the light source producing an incident light wave propagating towards the sample along a propagation axis;
   acquiring, using a matrix-array photodetector, a single image of the sample, the sample being placed between the light source and the matrix-array photodetector such that the matrix-array photodetector is exposed to a light wave comprising interference between the incident light wave and a diffraction wave produced by the cell;
   identifying a position of the cell in a plane parallel to a detection plane in which the matrix-array photodetector lies;
   applying a digital reconstruction algorithm to the single acquired image, to determine at least one characteristic quantity of the light wave to which the matrix-array photodetector is exposed, at the position of the cell, at a plurality of reconstruction distances from the matrix-array photodetector along the propagation axis, the digital reconstruction algorithm comprising performing a convolution product based on the acquired image and a propagation operator, the propagation operator describing the propagation of the light between the matrix-array photodetector and each reconstruction distance;
   obtaining a profile representing a variation of the characteristic quantity as a function of the distance along the propagation axis, the profile being obtained using the single acquired image; and
   classifying the cell depending on the profile, the classification allowing the state of the cell to be determined from among preset states.

2. The method of claim 1, wherein the preset states comprise a living cell state and/or a dead cell state.

3. The method of claim 1, wherein the characteristic quantity is obtained by estimating, at each reconstruction distance, a complex expression of the light wave to which the matrix-array photodetector is exposed.

4. The method of claim 3, wherein the characteristic quantity is determined from the modulus or the argument of the complex expression.

5. The method of claim 1, wherein the classification is carried out by comparing variation in the characteristic quantity to preset reference profiles.

6. The method of claim 1, further comprising reconstructing an image of the characteristic quantity in a plane parallel to the detection plane, and at the reconstruction distance, the value of the characteristic quantity at the position of the cell, at the reconstruction distance, being determined depending on this image.

7. The method of claim 1, wherein the position of each cell, in a plane parallel to the detection plane, is determined using the image thus reconstructed.

8. The method of claim 1, further comprising:
determining a reference complex image, in a reconstruction plane or in the detection plane, by applying a digital reconstruction algorithm to the image acquired by the matrix-array photodetector; and
based on the reference complex image, estimating at least one characteristic quantity of the light wave to which the matrix-array photodetector is exposed, at a plurality of reconstruction distances from the matrix-array photodetector.

9. The method of claim 8, further comprising:
applying a propagation operator to the reference complex image, to calculate secondary complex images for a plurality of distances from the reconstruction plane or from the plane in which the matrix-array photodetector lies; and
determining a characteristic quantity at each of the reconstruction distances, from each secondary complex image.

10. The method of claim 1, wherein the light source is a spatially coherent source.

11. The method of claim 1, wherein the light source is a light-emitting diode.

12. The method of claim 1, wherein no magnifying optics are placed between the sample and the matrix-array photodetector.

13. A device for determining a state of a cell, the cell being placed in a sample, the device comprising:
a light source configured to produce an incident light wave, along a propagation axis, in a direction of the sample;
a matrix-array photodetector configured to acquire a single image of the sample, on being exposed to a light wave resulting from interference between the incident light wave and a diffraction wave formed by the cell;
a holder to hold the sample between the light source and the matrix-array photodetector;
a processor configured to:
identify a position of the cell in a plane parallel to a plane in which the photodetector lies;
apply a digital reconstruction algorithm to the single acquired image, to determine at least one characteristic quantity of the light wave to which the photodetector is exposed, at the position, at a plurality of reconstruction distances from the photodetector along the propagation axis, the digital reconstruction algorithm comprising a convolution product based on the acquired image and a propagation operator, the propagation operator describing the propagation of the light between the matrix-array photodetector and each reconstruction distance;
obtain a profile representing a variation of the characteristic quantity as a function of the distance along the propagation axis, the profile being obtained using the single acquired image; and
classify the cell depending on the profile, the classification allowing to determine the state of the cell from among preset states.

14. The device of claim 13, wherein the device comprises no magnifying optics between the photodetector and the sample.

15. An incubator, for growth of cells, the incubator comprising at least one device of claim 13.

* * * * *